United States Patent [19]

Thomason

[11] Patent Number: 5,705,484
[45] Date of Patent: Jan. 6, 1998

[54] BIOLOGICALLY ACTIVE POLYPEPTIDE FUSION DIMERS

[75] Inventor: Arlen R. Thomason, Thousand Oaks, Calif.

[73] Assignee: Amgen Inc., Thousand Oaks, Calif.

[21] Appl. No.: 445,847

[22] Filed: May 22, 1995

Related U.S. Application Data

[63] Continuation of Ser. No. 41,635, Apr. 1, 1993, abandoned.

[51] Int. Cl.$^6$ .......................... C07K 14/49; C12N 15/18; A61K 38/18
[52] U.S. Cl. ..................... 514/12; 530/350; 530/399; 536/23.4; 435/69.7; 435/325
[58] Field of Search ..................... 530/350, 399; 514/12; 435/69.1, 320.1, 340.2, 252.33, 252.3, 255.1, 255.2, 325; 536/23.4

[56] References Cited

U.S. PATENT DOCUMENTS 4,766,073  8/1988  Murray et al. ................. 435/172.3

FOREIGN PATENT DOCUMENTS

| 0 225 579 | 6/1987 | European Pat. Off. . |
| 0 259 632 | 3/1988 | European Pat. Off. . |
| 0 325 224 | 7/1989 | European Pat. Off. . |

OTHER PUBLICATIONS

Hoppe, J. et al., *Eur. J. Biochem.*, 187 (1): 207–214, 1990.
Andersson, M. et al., *J. Biol. Chem.*, 267 (16): 11260–11266, 1992.
J. Hoppe et al., Preparation of biologically active platelet–derived growth factor isoforms AA and AB, *Eur. J. Biochem.*, 187 (1), 207–214 (1990).
Andersson et al., Assignment of Interchain Disulfide Bonds in Platelet–derived Growth Factor (PDGF) and Evidence for Agonist Activity of Monomeric PDGF, *J. Biol. Chem.*, 267 (16), 11260–11265 (1990).
Qian, S.W. et al., Identification of the structural doman that distinguishes the actions of the type 1 and 2 isoforms of transforming growth factor β on endothelial cells, *Proc. Natl. Acad. Sci. USA*, (89), (1992).
Brinkmann et al., Independent domain folding of Pseudomonas exotoxin and single–chain immunotixins: Influence of interdomain connections, *Proc.Natl.Acad.Sci. USA*, (89) (1992).
Geisow, M.J., Molecular couturiers and designer proteins, *Tibtech*, (11) (1993).

*Primary Examiner*—Marianne P. Allen
*Attorney, Agent, or Firm*—Joan D. Eggert; Ron K. Levy; Steven M. Odre

[57] ABSTRACT

The present invention provides a biologically active multimeric polypeptide molecule in which two or more monomeric subunits are linked together as a single polypeptide ("fusion multimer"). These fusion multimers are more easily and rapidly refolded than unfused multimers, because the reactions necessary to generate the biologically active multimeric form of the polypeptide proceed with first order, rather than second or higher order, reaction kinetics. Fusion multimers also eliminate the simultaneous formation of undesired polypeptide by-products during refolding. The fusion multimers of the present invention specifically include PDGF fusion dimers.

17 Claims, 7 Drawing Sheets

SerLeuGlySerLeuThrIleAlaGluProAlaMetIleAlaGluCysLysThrArgThr
GluValPheGluIleSerArgArgLeuIleAspArgThrAsnAlaAsnPheLeuValTrp
ProProCysValGluValGlnArgCysSerGlyCysCysAsnAsnArnAsnValGlnCys
ArgProThrGlnValGlnLeuArgProValGlnLeuLysIleGluIleValArgLys
LysProIlePheLysLysAlaThrValThrLeuGluAspHisLeuAlaCysLysCysGlu
ThrValAlaAlaAlaArgProValThrArgSerProGlyGlySerGlnGluGlnArgGlu
<u>LeuTyrLysMetLeuSerGlyHisSerIleArgSerPheAspAspLeuGlnArgLeuLeu</u>
<u>GlnGlyAspSerGlyLysGluGluSerLeuAlaGluLeuAspLeuAsnMetThrArgSerHis</u>
<u>SerGlyGlyGluLeuGluSerLeuAlaArgGlyLysArg</u>SerLeuGlySerLeuThrIle
AlaGluProAlaMetIleAlaGluCysLysThrArgThrGluValPheGluIleSerArg
ArgLeuIleAspArgThrAsnAlaAsnPheLeuValTrpProProCysValGluValGln
ArgCysSerGlyCysCysAsnAsnArgAsnValGlnCysArgProThrGlnValGlnLeu
ArgProValGlnLeuArgLysIleGluIleValArgLysLysProIlePheLysLysAla
ThrValThrLeuGluAspHisLeuAlaCysLysCysGluThrValAlaAlaAlaArgPro
ValThr

FIG. 1

```
            10                  30                  50
CTAGAAGGAGGAATAACATATGTCTCTGGGTTCGTTAACCATTGCGGAACCGGCTATGAT
1   -----+---------+---------+---------+---------+---------+  60
    TTCCTCCTTATTGTATACAGAGACCCAAGCAATTGGTAACGCCTTGGCCGATACTA
                  MetSerLeuGlySerLeuThrIleAlaGluProAlaMetIl
                  1
            70                  90                 110
    TGCCGAGTGCAAGACACGAACCGAGGTGTTCGAGATCTCCCGGCGCCTCATCGACCGCAC
61  ---------+---------+---------+---------+---------+---------+ 120
    ACGGCTCACGTTCTGTGCTTGGCTCCACAAGCTCTAGAGGGCCGCGGAGTAGCTGGCGTG
    eAlaGluCysLysThrArgThrGluValPheGluIleSerArgArgLeuIleAspArgTh
    14
            130                 150                170
    CAATGCCAACTTCCTGGTGTGGCCGCCCTGCGTGGAGGTGCAGCGCTGCTCCGGCTGTTG
121 ---------+---------+---------+---------+---------+---------+ 180
    GTTACGGTTGAAGGACCACACCGGCGGGACGCACCTCCACGTCGCGACGAGGCCGACAAC
    rAsnAlaAsnPheLeuValTrpProProCysValGluValGlnArgCysSerGlyCysCy
    34
            190                 210                230
    CAACAACCGCAACGTGCAGTGCCGGCCCACCCAGGTGCAGCTGCGGCCAGTCCAGGTGAG
181 ---------+---------+---------+---------+---------+---------+ 240
    GTTGTTGGCGTTGCACGTCACGGCCGGGTGGGTCCACGTCGACGCCGGTCAGGTCCACTC
    sAsnAsnArgAsnValGlnCysArgProThrGlnValGlnLeuArgProValGlnValAr
    54
            250                 270                290
    AAAGATCGAGATTGTGCGGAAGAAGCCAATCTTTAAGAAGGCCACGGTGACGCTGGAGGA
241 ---------+---------+---------+---------+---------+---------+ 300
    TTTCTAGCTCTAACACGCCTTCTTCGGTTAGAAATTCTTCCGGTGCCACTGCGACCTCCT
    gLysIleGluIleValArgLysLysProIlePheLysLysAlaThrValThrLeuGluAs
    74
            310                 330                350
    CCACCTGGCATGCAAGTGTGAGACAGTGGCAGCTGCACGGCCTGTGACCCGAAGCCCGGG
301 ---------+---------+---------+---------+---------+---------+ 360
    GGTGGACCGTACGTTCACACTCTGTCACCGTCGACGTGCCGGACACTGGGCTTCGGGCCC
    pHisLeuAlaCysLysCysGluThrValAlaAlaAlaArgProValThrArgSerProGl
    94
            370        380
    GGGTTCCCAGGAGCAGCGATAAG
361 ---------+---------+--- 
    CCCAAGGGTCCTCGTCGCTATTCTTAA
    yGlySerGlnGluGlnArg
    114                   1195
```

FIG. 3

```
              10                    30                    50
               .                     .                     .
TCGACAGTCGGCATGAATCGCTGCTGGGCGCTCTTCCTGTCTCTCTGCTGCTACCTGCGT
              MetAsnArgCysTrpAlaLeuPheLeuSerLeuCysCysTyrLeuArg 70                    90                    110
               .                     .                     .
CTGGTCAGCGCCGAGGGGGACCCCATTCCCGAGGAGCTCTATAAGATGCTGAGTGGCCAC
LeuValSerAlaGluGlyAspProIleProGluGluLeuTyrLysMetLeuSerGlyHis 130                   150                   170
               .                     .                     .
TCGATTCGCTCCTTCGATGACCTCCAGCGCCTGCTGCAGGGAGACTCCGGAAAAGAAGAT
SerIleArgSerPheAspAspLeuGlnArgLeuLeuGlnGlyAspSerGlyLysGluAsp 190                   210                   230
               .                     .                     .
GGGGCTGAGCTGGACCTGAACATGACCCGCTCCCATTCTGGTGGCGAGCTGGAGAGCTTG
GlyAlaGluLeuAspLeuAsnMetThrArgSerHisSerGlyGlyGluLeuGluSerLeu 250                   270                   290
               .                     .                     .
GCTCGTGGGAAAAGGAGCCTGGGTTCGTTAACCATTGCGGAACCGGCTATGATTGCCGAG
AlaArgGlyLysArgSerLeuGlySerLeuThrIleAlaGluProAlaMetIleAlaGlu 310                   330                   350
               .                     .                     .
TGCAAGACACGAACCGAGGTGTTCGAGATCTCCCGGCGCCTCATCGACCGCACCAATGCC
CysLysThrArgThrGluValPheGluIleSerArgArgLeuIleAspArgThrAsnAla 370                   390                   410
               .                     .                     .
AACTTCCTGGTGTGGCCGCCCTGCGTGGAGGTGCAGCGCTGCTCCGGCTGTTGCAACAAC
AsnPheLeuValTrpProProCysValGluValGlnArgCysSerGlyCysCysAsnAsn 430                   450                   470
               .                     .                     .
CGCAACGTGCAGTGCCGGCCCACCCAGGTGCAGCTGCGGCCAGTCCAGGTGAGAAAGATC
ArgAsnValGlnCysArgProThrGlnValGlnLeuArgProValGlnValArgLysIle 490                   510                   530
               .                     .                     .
GAGATTGTGCGGAAGAAGCCAATCTTTAAGAAGGCCACGGTGACGCTGGAGGACCACCTG
GluIleValArgLysLysProIlePheLysLysAlaThrValThrLeuGluAspHisLeu 550                   570
               .                     .
GCATGCAAGTGTGAGACAGTGGCAGCTGCACGGCCTGTGACCTGATAA
AlaCysLysCysGluThrValAlaAlaAlaArgProValThr
```

FIG. 4

BIOLOGICALLY ACTIVE POLYPEPTIDE FUSION DIMERS

This application is a continuation of application Ser. No. 08/041,635 now abandoned filed Apr. 1, 1993 which is hereby incorporated by reference.

BACKGROUND

Human platelet-derived growth factor ("PDGF") is believed to be the major mitogenic growth factor in serum for connective tissue cells. The mitogenic activity of PDGF has been documented in numerous studies, wherein PDGF has been shown to positively affect mitogenesis in arterial smooth muscle cells, fibroblast cells lines, and glial cells. Deuel et al., *J. Biol. Chem.*, 256(17), 8896–8899 (1981). See also, e.g., Heldin et al., *J. Cell Physiol.*, 105, 235 (1980) (brain glial cells); Raines and Ross, *J. Biol. Chem.*, 257, 5154 (1982) (monkey arterial smooth muscle cells). PDGF is also believed to be a chemoattractant for fibroblasts, smooth muscle cells, monocytes, and granulocytes. Because of its apparent abilities to both induce mitogenesis at the site of connective tissue wounds, and to attract fibroblasts to the site of such wounds, PDGF is thought to have particular potential for therapeutic use in the repair of injured, or traumatized, connective tissues.

Other members of the PDGF family include vascular endothelial cell growth factor ("VEGF", sometimes also referred to as "vascular permeability factor, or "VPF") and placental growth factor ("PLGF"). Tischer et al., *Biochem. Biophys. Res. Comm.*, 165(3), 1198–1206 (1989) and Maglione et al., *Proc. Natl Acad Sci. USA*, 88, 9267–9271 (1991), respectively. Both VEGF and PLGF form disulfide bonded dimers from the eight highly conserved cysteine residues that appear in the PDGF homologous region of each monomeric unit of these PDGF family members. Tischer et al. and Maglione et al., ibid. The receptors for VEGF and PLGF are also in the same receptor subfamily as the PDGF receptors. Consequently, these "newer" members of the PDGF family are thought to be potentially useful as therapeutic products in wound repair, although they have not been studied as extensively as PDGF.

Naturally occurring PDGF is a disulfide-bonded dimer having two polypeptide chains, namely the "A" and "B" chains, with the A chain being approximately 60% homologous to the B chain. Naturally occurring PDGF is found in three dimeric forms, namely PDGF-AB heterodimer, PDGF-BB homodimer, or PDGF-AA homodimer. Hannink et al., *Mol. cell. Biol.*, 6, 1304–1314 (1986). Although PDGF-AB has been identified as the predominate naturally occurring form, it is the PDGF-BB homodimer that has been most widely used in wound healing studies. Each monomeric subunit of the biologically active dimer, irrespective of whether it is an A chain monomer or a B chain monomer, contains eight cysteine residues. Some of these cysteine residues form interchain disulfide bonds which hold the dimer together.

The PDGF-B found in human platelets has been identified as a 109 amino acid cleavage product (PDGF-$B_{109}$) of a 241 amino acid precursor polypeptide Johnsson et al., *EMBO Journal*, 3(5), 921–928 (1984). This 109 amino acid homologous sequence coincides with the 109 amino acid cleavage product of the c-sis encoded PDGF-B precursor protein and is believed by many to be the mature form of PDGF in humans. Homology with the c-sis encoded precursor protein begins at amino acid 82 of the 241 amino acid precursor protein and continues for 109 amino acids.

Another form of PDGF-B (PDGF-$B_{119}$), corresponding to the first 119 amino acids of the c-sis encoded PDGF-B precursor protein, has also been identified as a major cleavage product of the c-sis encoded precursor protein when the entire c-sis gene is encoded into a transfected mammalian host. U.S. Pat. No. 5,149,792. The region corresponding to amino acids 13–99 of the mature form of PDGF-B has been referred to as the "PDGF homologous region". See Tischer et al. and Maglione et al., ibid.

Recombinant PDGF has been produced in mammalian, yeast and bacterial (*E. coli*) host cells. See, European Patent Publication No. 0282317 (mammalian host cells), U.S. Pat. No. 4,766,073 (yeast host cells), and U.S. Pat. No. 5,149,792 (*E. coli* host cells). Both mammalian and yeast host cells assemble the dimeric molecules from the monomeric subunits in vivo, such that the protein is expressed in its biologically active dimeric form. Bacterial host cells such as *E. coli*, on the other hand, synthesize PDGF monomers. These individual monomeric subunits must then be isolated and refolded, requiring further in vitro processing steps, in order to obtain the desired dimeric form of the polypeptide.

The more highly evolved mammalian and yeast host cell systems are desirable for their ability to produce multimeric polypeptides in their biologically active multimeric form, although the secretion levels of the desired recombinant product are relatively low as compared with the secretion levels of bacterial host cells. The trade-off with the higher expressing bacterial systems, such as *E. coli*, is that, in return for obtaining higher yields of recombinant product, the recombinant protein must be isolated from inclusion bodies and, in the case of a multimeric protein such as PDGF, refolded in order to generate biologically active product.

Although recently developed refolding methods, such as described in European Patent Publication no. 0460189, have increased the desirability of producing PDGF in bacterial host cells, there still remain as obstacles decreased yields during refolding (resulting from higher order reaction kinetics) and the formation of undesired polypeptide by-products where a heterodimer, or a homodimer having different analog subunits of the same PDGF chain, is refolded. (See, e.g., European Patent Publication No. 0460189, ibid, wherein a PDGF-AB heterodimer formed by refolding PDGF-A and PDGF-B monomeric subunits obtained from two different transfected bacterial host cells also resulted in the formation of homodimeric PDGF-AA and PDGF-BB by-product.)

It is an object of the present invention to provide a multimeric polypeptide having improved refolding kinetics.

It is a further object of the present invention to provide a multimeric polypeptide that can be produced recombinantly without the formation of undesired polypeptide by-products.

SUMMARY OF THE INVENTION

The present invention provides a biologically active polypeptide molecule in which at least two monomeric polypeptide subunits of a naturally occurring multimeric protein are linked together as a single polypeptide ("fusion multimer"). The polypeptide is preferably a dimeric polypeptide from the PDGF family. The fusion multimers of the present invention are more easily and rapidly refolded than unfused multimers, because the reactions necessary to generate the biologically active multimeric form of the polypeptide proceed with first order, rather than second or higher order, reaction kinetics. The fusion multimers of the present invention also eliminate the simultaneous formation of undesired polypeptide by-products during refolding. The individual subunits of the fusion multimer of the present invention are linked together in a head to tail manner. The individual subunits may be linked together directly, or they may be separated by a spacer moiety.

The present invention also provides a method for making a biologically active fusion multimer by transfecting a host cell with a DNA sequence having the respective coding sequences of each monomeric subunit of the fusion multimer linked together in a head to tail manner to form a single continuous polypeptide.

BRIEF DESCRIPTION OF THE DRAWINGS

FIG. 1 is the amino acid sequence of a PDGF fusion dimer, in which a PDGF-$B_{119}$ subunit is linked to a PDGF-$B_{109}$ subunit, separated by a spacer of amino acids $-54$ to $-1$ of the pre-pro region of the PDGF-B precursor protein. (SEQ ID NO. 1)

FIG. 3 is a nucleic acid coding sequence for PDGF-$B_{119}$. (SEQ ID NO. 3)

FIG. 4 is a nucleic acid coding sequence for PDGF-$B_{109}$ preceded by the entire pre-pro region (81 amino acids) of the PDGF-B precursor protein.

DETAILED DESCRIPTION OF THE INVENTION

Figure 2A:
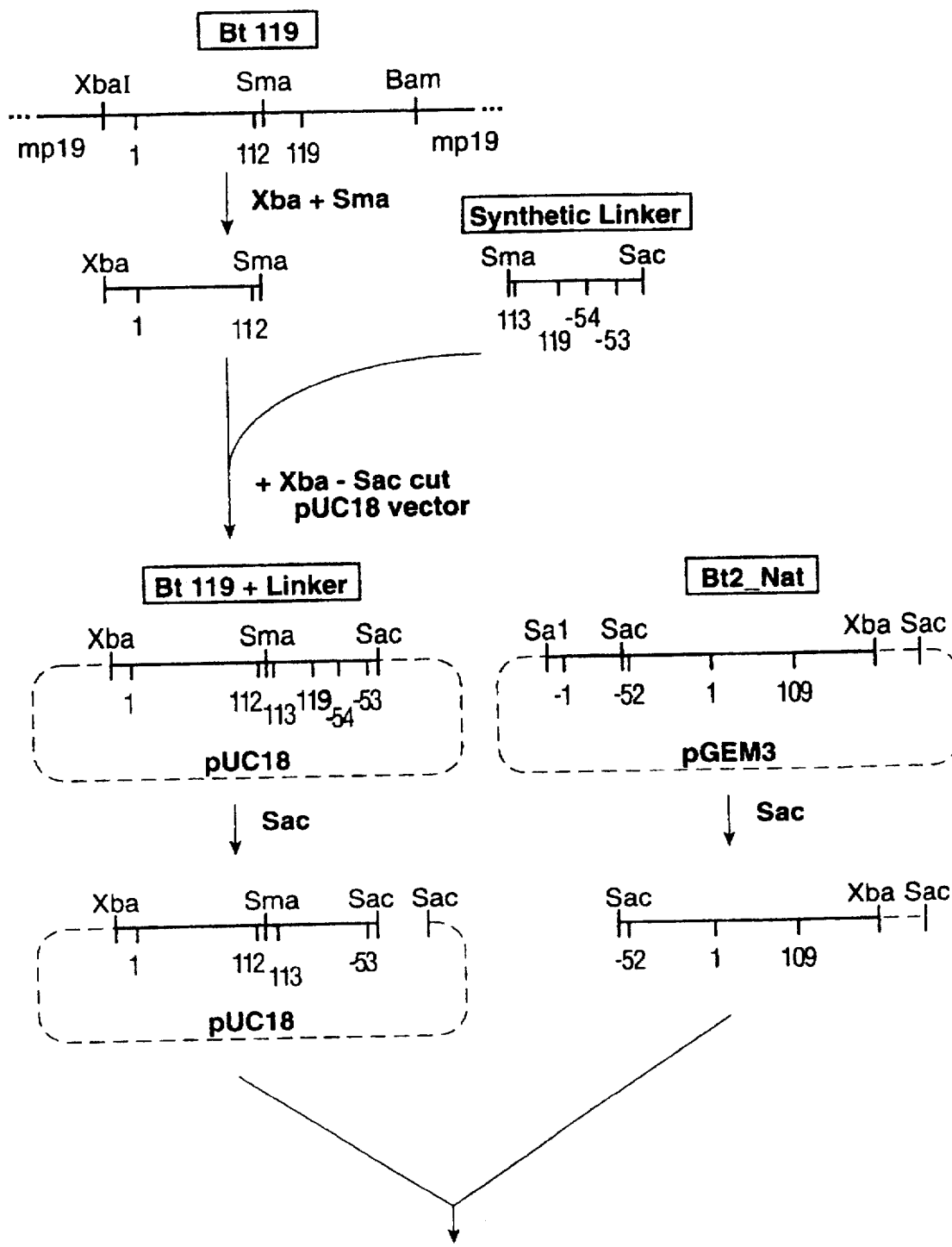
FIG. 2 is a diagram of the steps used in construction an expression plasmid coding for the production of the PDGF-$B_{119}B_{109}$ fusion dimer shown in FIG. 1. (SEQ ID NO. 2)

The present invention provides a biologically active polypeptide molecule in which at least two monomeric polypeptide subunits of a naturally occurring multimeric protein are linked together as a single polypeptide ("fusion multimer"). Preferably, the fusion multimer is a member of the PDGF family.

In order to aid in the understanding of the present invention, the following terms, as used herein, have the definitions designated below.

The terms "multimer" or "multimeric" polypeptide refer to a polypeptide molecule which, in its natural, biologically active form, contains more than one functional polypeptide subunit. The functional monomeric subunits may be covalently bonded to each other, such as through disulfide bonding, but can be separated by subjecting the multimeric polypeptide to reducing conditions, thus breaking the disulfide bonds.

The terms "dimer" or "dimeric" polypeptide refer to a polypeptide molecule which, in its natural, biologically active form, contains two functional subunits.

The terms "monomer" and "monomeric" polypeptide or "monomeric" subunit refer to a single subunit of a multimeric polypeptide. The monomeric subunit may be an exact copy of the naturally occurring monomeric subunit or it may be either a biologically active analog or a biologically inactive (inhibitor) analog. It will be appreciated that a "reduced" polypeptide will necessarily be monomeric, unless it is a fusion dimer.

The term "fusion multimer" means a polypeptide which, in its naturally occurring, biologically active form exists as a multimer, but which has been engineered to have its constituent monomeric subunits linked together, either directly, or through a spacer moiety, as a single continuous polypeptide.

The term "fusion dimer" means a polypeptide which, in its naturally occurring, biologically active form exists as a dimer, but which has been engineered to have its two constituent monomeric subunits linked together, either directly or through a spacer moiety as a single continuous polypeptide.

As used herein, the term "homodimer" refers to a dimeric molecule wherein each monomeric subunit is either the same as or is an analog of the same naturally occurring monomeric subunit. For example, PDGF is known to have several mature forms. Therefore, a PDGF-$B_{109}B_{119}$ dimer is considered to be a PDGF-BB homodimer even though the monomeric subunits are not exactly the same.

The term "spacer moiety" means a polypeptide amino acid sequence separating two monomeric subunits in a fusion multimer.

The term "biologically active" polypeptide means a polypeptide having substantially the same mitogenic, chemotactic, enzymatic and/or other detectable biological activity as the corresponding naturally occurring polypeptide.

The term "inhibitor" analog or "inhibitor" polypeptide means a biologically inactive polypeptide that inhibits the mitogenic, chemotactic, enzymatic and/or other detectable biological activity of the corresponding naturally occurring polypeptide.

As used herein, "refolding" means bringing a denatured, reduced or partially reduced polypeptide into a biologically active conformation. Refolding includes those instances wherein a polypeptide has been produced in denatured form and is, in fact, being brought into a biologically active conformation for the first time. The term "refolding" may be used interchangeably with "folding".

As used herein, "interchain disulfide bond" is a disulfide bond formed between two cysteine moieties of a dimeric polypeptide, wherein the cysteine moieties which form the disulfide bond are from different monomeric subunits.

As used herein, "intrachain disulfide bond" is a disulfide bond formed between two cysteine moieties of a dimeric polypeptide, wherein the cysteine moieties which form the disulfide bond are from the same monomeric subunit.

Unless otherwise specified, PDGF is any combination of PDGF monomers and/or dimers, including analogs thereof, reduced or unreduced, biologically active, or inactive, recombinant or otherwise. The term "PDGF" is intended to include PDGF analogs having one or more modifications to the number and/or identity of amino acid sequences of naturally occurring PDGF.

The term "PDGF homologous region" means the amino acid sequence from amino acid 13 to amino acid 99 in naturally occurring PDGF-B.

The term "PDGF family" means a naturally occurring dimeric polypeptide having at least about 20% amino acid sequence homology to the PDGF homologous region and having a total of eight cysteine residues within the PDGF homologous region such that the cysteine residues are highly conserved.

As used herein, cysteine residues that are "highly conserved" within the PDGF family refer to cysteine residues within the PDGF homologous region wherein no more than five adjustments, in terms of additions or deletions of numbers of amino acids, must be made in order to exactly line up the cysteine residues within the PDGF homologous sequence of a PDGF family member to the cysteine residues within the PDGF homologous region of naturally occurring PDGF B.

The term "PDGF precursor protein" refers to the entire 241 amino acid c-sis-encoded precursor protein prior to processing of the polypeptide to its shorter, mature forms (e.g., PDGF-$B_{109}$ and PDGF-$B_{119}$).

The term "pre-pro" region means that portion of the PDGF precursor protein which lies to the amino terminal side of the mature PDGF protein. Using the numbering system of Devare et al, (Devare et al., *Proc. Natl Acad. Sci. USA*, 80, 732 (1983) the pre-pro region extends from amino acid −81 to amino acid −1, with the remaining amino acid sequence from 1 to 160 representing amino acids found in various mature forms of PDGF, the most common of which being PDGF-$B_{109}$ (amino acids 1-109) and PDGF-$B_{119}$ (amino acids 1-119).

The fusion multimer of the present invention may be any polypeptide which, in its naturally occurring, biologically active form, exists as a multimer, but which has been engineered in accordance with the teachings of the present invention to have its constituent monomeric subunits linked together, either directly, or through a spacer moiety, as a single continuous polypeptide.

The fusion multimers of the present invention virtually eliminate the simultaneous formation of undesired polypeptide by-products during refolding. This is particularly important where high expression bacterial host cells are used for the expression of a recombinant multimeric protein. For example, in the case where a PDGF-AB heterodimer is refolded from PDGF-A and PDGF-B monomeric subunits generated from two different *E. coli* host strains, the undesired PDGF-AA and PDGF-BB homodimeric forms must be separated from the desired PDGF-AB heterodimeric product. (European Patent Publication No. 0460189, ibid.) In contrast, if a PDGF-AB fusion heterodimer is expressed as a single continuous polypeptide from an *E. coli* host, in accordance with the teachings of the present invention, no such polypeptide by-products are formed. This provides a tremendous benefit in the commercial production of large quantities of multimeric proteins.

The same benefit can also be applicable to mammalian and yeast host cells, because these higher level expression systems have also been known to secrete undesired polypeptide by-products in certain situations where multimeric proteins are desired. The fusion multimer of the present invention essentially eliminates the formation of these unwanted by-products.

The fusion multimers of the present invention are expected to be more easily and rapidly refolded than unfused multimers, because the reactions necessary to generate the biologically active multimeric form of the fusion polypeptide proceed with first order reaction kinetics. Unfused multimeric polypeptides, on the other hand, typically refold according to second or higher order reaction kinetics. The ability to reduce the forces necessary to bring together the two or more subunits required for refolding of the desired multimeric protein into its biologically active conformation should hasten the refolding process considerably.

The fusion multimers of the present invention can also be engineered to act as inhibitor polypeptides. This is possible, because many multimeric polypeptides function by interacting simultaneously in some way with more than one target molecule. If a fusion multimer is designed to contain at least one inhibitor analog as a monomeric subunit, the resulting multimeric inhibitor polypeptide can interact with one, but not more than one, available target molecule simultaneously. The resulting "non-productive" interaction will reduce the number of target molecules available for productive interaction with the naturally occurring biologically active form of the multimeric protein so that it cannot function to bring about its normal biological response.

An intervening region, otherwise referred to as a "spacer" or "spacer moiety", may or may not be necessary for proper folding in the case of certain fusion multimers. A spacer moiety will ordinarily be used where it is believed that the presence of a spacer will allow greater freedom for the constituent monomeric subunits of a fusion multimer to interact with each other in order to generate a biologically active form of the folded multimeric protein.

If the fusion multimer is intended for use as a human therapeutic product and a spacer moiety is desired, it is preferable to select the spacer moiety from among human polypeptides, because these polypeptide sequences will have much less of a chance of inducing an immune reaction than will a foreign polypeptide sequence. The polypeptide sequence for the spacer moiety may be any number of amino acids long, provided that the spacer moiety is not so long and cumbersome as to interfere with the necessary interaction between the constituent monomeric subunits of the fusion dimer. It will also be preferred to avoid amino acid residues that are known to interact with other residues (e.g., cysteine residues) and amino acids that are may create unusual twists or turns in an amino acid sequence.

The fusion multimer of the present invention is preferably a dimeric member of the PDGF family. More preferably, the fusion dimer is a dimeric form of PDGF, VEGF, or PLGF. Still more preferably, the fusion dimer is a dimeric form of PDGF. Most preferably, the fusion multimer of the present invention is a PDGF-BB fusion dimer. The preferred PDGF-BB fusion dimer may be a biologically active polypeptide or an inhibitor polypeptide.

In the case of a PDGF fusion dimer, a spacer moiety is not believed to be necessary. Nevertheless, if a spacer moiety is desired in the case of a PDGF fusion dimer, it will be preferable to use a spacer moiety selected from a portion of the c-sis encoded PDGF precursor protein. More preferably selection of the spacer moiety will be from the "pre-pro" region of the PDGF precursor protein. The pre-pro region of the PDGF precursor protein in the amino terminal end of the protein beginning with amino acid −81 and ending with amino acid −1. This is the region of the PDGF precursor protein that is usually cleaved off during processing by host cells transfected with the entire v-sis or c-sis coding sequence, and is not expected to interfere with the refolding of the PDGF fusion dimer or contribute errant properties of its own to the fusion dimer. Importantly, the pre-pro region of the PDGF precursor protein does not contain any cysteine residues.

A biologically active fusion dimer was made according to the present invention using two PDGF-B chains connected through a spacer moiety consisting of a portion of the "pre-pro" region of the PDGF B precursor protein. Although the spacer moiety is not believed to be necessary to generate a biologically active PDGF-BB fusion dimer, this particular fusion polypeptide was conveniently made from available starting materials and demonstrated biological activity.

The existence of biological activity in a fusion multimer, such as the PDGF-BB fusion dimer, demonstrated in the examples which follow, was somewhat surprising in light of the fact that there is no precedent for making a biologically active fusion dimer. Although fusion proteins (employing a highly expressing protein at the amino terminus) have been known to be effective in improving the expression of polypeptides generated for the purpose of inducing antibody response, these fusion proteins are not required to have biological activity, but merely to have epitopes for recognition by antibodies. Also, it has been suggested that the joining of two different but related proteins into a single fusion protein may result in a synergistic effect not observed when the two proteins act independently in their naturally occurring, unfused form. (Williams and Park, *Cancer*, 67, 2705–2707 (1991; granulocyte-macrophage colony-stimulating factor and interleukin-3 prepared as fusion protein). However, there is no suggestion that two monomeric subunits which must interact directly to exhibit biological activity in nature can be linked together in a single continuous polypeptide yet retain the ability to perform the same necessary interactions required for biological activity of the resulting fusion multimer.

The present invention also provides a method for making a biologically active fusion multimer by transfecting a host cell with a DNA sequence having the respective coding sequences of each monomeric subunit of the multimeric polypeptide linked together in a head to tail manner to code for a single continuous polypeptide. (I.e., the subunits are not separated by start and stop codons.) If a spacer moiety is desired in the fusion dimer product, a coding sequence for the spacer moiety is inserted between the coding sequences for the constituent monomeric subunits.

The fusion multimer of the present invention can generally be made by any one of a number of methods known to those skilled in the art for the production of recombinant proteins. In many cases, the coding sequences for the monomeric subunits of the fusion dimer may already be available. These subunits can be easily linked together, with or without a spacer, through a DNA linker using standard linking techniques known to those skilled in the art. It is also, or course, possible to synthesize the desired fusion multimer coding sequence using a DNA sequenator. The particular method used to generate the coding sequence for the fusion dimer will ordinarily be dictated by a number of practical considerations including the availability of starting materials. Once the coding sequence for the fusion multimer product is constructed, it is inserted into a vector, with the resulting vector being used to transfect a suitable host cell using standard techniques known to those skilled in the art.

In the case of a PDGF-BB fusion homodimer, for example, one can first modify the v-sis gene to obtain the human counterpart c-sis, or use c-sis as a starting material. Two of the modified coding sequences are then linked together, following placement of appropriate initiation and stop codons, and inserted into a suitable vector which is then used to transfect the desired host cell.

Alternatively, one can either synthesize the PDGF-BB fusion homodimer coding sequence, or first cut back the c-sis gene or modified v-sis gene, at an appropriate restriction site near the carboxy terminus, and then rebuild the carboxy terminus of the PDGF precursor protein coding sequence to the desired end position using preferred codons for the particular vector and host cell being employed. The c-sis gene or modified v-sis gene can also be cut back at an appropriate restriction site near the amino terminus, with the amino terminus being built back to the desired starting position, again using preferred codons for the selected vector and host cell systems. In other words, any combination of synthetic methods and in vitro mutagenesis of naturally occurring staring materials can be used to generate fusion multimers, such as the PDGF-BB fusion dimer.

In the preferred method for generating the PDGF-BB fusion dimer of the present invention, the v-sis gene is modified to obtain the c-sis gene, otherwise referred to as the PDGF-B precursor protein coding sequence. The PDGF-B precursor protein coding sequence is then modified to obtain the desired coding sequences for the two monomeric units of the PDGF-BB fusion dimer, each of which will preferably be smaller than the entire 241 amino acid PDGF-B precursor protein. These units may be identical, or they may slightly different. For example, it is possible to construct a PDGF-$B_{119}B_{109}$ fusion homodimer wherein one monomeric subunit is the 119 amino acid form of PDGF-B and the other subunit is the 109 amino acid form of PDGF-B. It will typically be preferred, but not essential, that the monomeric units of a PDGF-BB fusion homodimer begin about amino acid 1 of and end between about amino acid 109 and amino acid 119 of the PDGF precursor protein. The coding sequences for the desired two monomeric subunits are then linked together at desired locations, with or without a spacer.

The v-sis gene provides an excellent starting material for obtaining a precursor protein coding sequence which can then be used to generate coding sequences for the desired monomeric subunits of a PDGF-BB fusion homodimer according to the present invention. For example, in the region coding for amino acids 1-119, there are only five amino acid differences between the protein encoded by the v-sis gene and the c-sis encoded PDGF-B precursor protein. Two of these five amino acids in the v-sis gene can be altered by in vitro mutagenesis techniques to generate a DNA sequence coding for a protein in which the two amino acids are the same as the corresponding residues in the PDGF-B precursor protein. A number of methods for in vitro mutagenesis of DNA can be utilized for introducing the desired changes in codons 101 and 107. Such methods are will known to those skilled in the art. For example, the method of Eckstein and co-workers (Taylor et al., *Nucl. Acids Res.*, 13, 8764–8785 (1985); Nakamae and Eckstein, *Nucl. Acids Res.*, 14, 9679–9698 (1986)), as described in the instruction booklet for the Amersham (Arlington Heights, Ill.) "Oligonucleotide-Directed In Vitro Mutagenesis System: kit, is particularly useful in converting the isoleucine residue at amino acid 101 to a threonine residue, and the alanine residue at amino acid 107 to a proline residue.

Following in vitro mutagenesis of amino acids 101 and 107, the altered v-sis DNA may then be cut back at the amino terminus with the restriction enzyme BglII, which cuts at a position corresponding to amino acid 24. The upstream portion of the gene, including the first 24 amino acids, may be restored by ligation of the downstream, BglII-cut mutagenized v-sis DNA with a synthetic DNA fragment encoding: (1) an ATG translation initiation codon; (2) a serine residue at amino acid 1; and, (3) the remainder of the first 24 amino acids of the c-sis encoded precursor protein. In this way, two of the other three variant amino acids, i.e., the serine residue at amino acid 6 and the valine residue at amino acid 7, will be converted to the human PDGF-B forms (threonine and isoleucine, respectively), with the upstream precursor amino acids encoded by v-sis being removed.

If a PDGF-B monomeric unit longer than amino acid 113 of the PDGF-B precursor protein is desired in the PDGF-B fusion dimer, the codon at amino acid position 114 of the v-sis gene must also be replaced with a codon coding for the appropriate amino acid in the PDGF-B precursor protein. This can be accomplished by cutting back from the carboxy terminus of the modified v-sis gene in a similar manner to that used to replace the codons for amino acids 101 and 107.

If the PDGF-B$_{119}$ form is desired as the second monomeric unit in the fusion dimer, the carboxy terminus can be replaced with a synthetic fragment that simultaneously alters amino acid 114 and replaces amino acid 120 with a stop codon. In this case, the mutagenized v-sis DNA is preferably cut with the restriction enzyme SmaI, which cuts at a position corresponding to amino acid 112. A synthetic DNA fragment coding for amino acids 112–119 of the PDGF-B precursor protein, and a translation stop codon at position 120 may then be ligated to the SmaI-cut mutagenized v-sis DNA. This synthetic DNA also encodes for a glycine residue, instead of a threonine residue, at amino acid 114, accomplishing the conversion of the fifth variant amino acid to the corresponding amino acid in the PDGF-B precursor protein.

To create the PDGF-BB fusion homodimer of the present invention, coding sequences for any two desired PDGF-B monomeric subunits are ligated together, with or without a spacer sequence, to generate the complete fusion dimer coding sequence. The complete coding sequence is then ligated into an appropriate expression vector, such as pCFM1156, and then transformed or transfected into an appropriate host cell system, preferably a bacterial host, such as *E. coli*. The N-terminal methionine may be removed in vivo following synthesis in the host cell, although some *E. coli* strains fail to remove the N-terminal methionine, thereby producing a recombinant product containing an additional amino acid residue at the amino terminus.

The preferred host cell system for production of the fusion dimer of the present invention is a bacterial host cell, preferably *E. coli*. In addition to the particular expression systems herein described, other systems are contemplated by the present invention and include, for example but without limitation, modification of the sites for protease cleavage, and/or use of an alternate leader sequence to increase the level of production of host cells of the fusion dimers of the present invention.

The therapeutic application of biologically active fusion dimers of the present invention can be used for the treatment of many types of wounds of mammalian species by physicians and/or veterinarians. The amount of biologically active PDGF used in such treatments will, of course, depend upon the severity of the wound being treated, the route of administration chosen, and the specific activity or purity of the fusion dimer, and will be determined by the attending physician or veterinarian. The term "fusion dimer therapeutically effective" amount refers to the amount of fusion dimer, in the absence of other exogenously applied growth factors, determined to produce a therapeutic response in a mammal. Such therapeutically effective amounts are readily ascertained by one of ordinary skill in the art.

The fusion dimer produced in accordance with the present invention may be administered by any route appropriate to the wound or condition being treated. Conditions which may be beneficially treated with therapeutic application(s) of PDGF fusion dimer include the aforementioned open dermal wound, dermal incisional wounds, and gastrointestinal incisional wounds. PDGF fusion dimer may also be used in the healing of bone, cartilage, tendons, ligaments, and epithelium (e.g., intestinal linings, stomach linings), and in glial repair.

Preferably, PDGF fusion dimer is applied exogenously to the wound. The exogenous application may be by a single application or dose, or by a repeated dose at multiple designated intervals. Compositions for exogenous application of the PDGF fusion dimer of the present invention are readily ascertained by one of ordinary skill in the art. It will be readily appreciated by those skilled in the art that the preferred route will vary with the wound or condition being treated. While it is possible for the PDGF fusion dimer to be administered as the pure or substantially pure compound, it is preferable to present it as a pharmaceutical formulation or preparation.

The formulations of the present invention, both for veterinary and for human use, comprise a therapeutically effective amount of PDGF as above described, together with one or more pharmaceutical acceptable carriers therefore and optionally other therapeutic ingredients. The carrier(s) must be "acceptable" in the sense of being compatible with the other ingredients of the formulation and not deleterious to the recipient thereof. Desirably, the formulation should not include oxidizing or reducing agents and other substances with which peptides are known to be incompatible. The formulations may conveniently be presented in unit dosage form and may be prepared by any of the methods well known in the art. All methods include the step of bringing into association the active ingredient with the carrier which constitutes on or more accessory ingredients. In general the formulations are prepared by uniformly and intimately bringing into association the fusion dimer with liquid carriers or finely divided solid carriers or both.

The following examples are provided to aid in the understanding of the present invention, the true scope of which is set forth in the appended claims. It is understood that modifications can be made in the procedures set forth, without departing from the spirit of the invention.

EXAMPLE 1

Construction of PDGF-B$_{119}$Coding Sequence

A PDGF-B$_{119}$ coding sequence, SEQ ID NO. 2 shown in FIG. 3, was constructed using the v-sis gene as a starting material.

A. Conversion of Amino acids 101 and 102

One microgram of the plasmid pC60, a clone of the simian sarcoma virus retroviral genome (Wong-Staal et al., *Science*, 213, 226–228 (1981)), was digested with restriction endonucleases SalI and XbaI, with the resulting 1183 base pair fragment then being purified by electrophoretic separation in a low melting temperature agarose gel, in accordance with the procedures described by Maniatis et al., *Molecular Cloning—A Laboratory Manual, Cord Spring Harbor Laboratory* (1982). The purified fragment was then excised from the gel. At the same time, 0.2 µg of M13mp19 DNA was also digested with SalI and XbaI, with the large 7245 base pair band being similarly isolated from a low melting temperature gel. Both excised gel slices were melted at 65° C., and then cooled to 37° C. All of the gel with the 7245 base pair M13mp19 fragment and one fourth of the gel with the 1183 base pair v-sis fragment were mixed and ligated according to Struhl, *Biotechniques*, 3, 452–453 (1985). The ligated DNA was transformed into *E. coli* K12 strain TG1, and a clear plaque was selected and grown in liquid culture. The presence of the 1183 base pair v-sis fragment in the M13mp19 vector was confirmed by preparation of the RF form of the phage DNA and restriction map analysis. Messing et al., *Nucl. Acids Res.*, 9, 309–321 (1981).

The M13mp19/v-sis phage thus obtained was grown in liquid culture, and the single stranded DNA isolated. Messing et al., ibid. This DNA was used as a template for oligonucleotide-directed in vitro mutagenesis to convert the amino acids at residues 101 and 107 to the corresponding amino acids of PDGF-B. I.e., the ATA codon coding for isoleucine 101 was converted to ACA (coding for threonine), and the GCT codon coding for alanine 107 was converted to CCT (coding for proline).

Ten micrograms of the M13mp19/v-sis single-stranded DNA was annealed with 8 pmol of a phosphorylated oligonucleotide having the sequence of SEQ ID NO. 4:

5' GGTCACAGGCCGTGCAGCTGCCACTGTCTCACAC 3'

This sequence is homologous to nucleotides 4283 to 4316 of the v-sis gene (numbering system of Devare, ibid). The underlined bases of the oligonucleotide denote the changes from the v-sis to the human PDGF-B sequence. DNA synthesis was initiated on the mutant oligonucleotide, with the complete mutant strand being synthesized with the Klenow fragment of E. coli DNA polymerase I using thionucleotide triphosphates, followed by ligation with T4 DNA ligase. Any remaining single-stranded template M13mp18/v-sis DNA was removed by filtration on nitrocellulose filters. The non-mutant strand was nicked by incubation with restriction endonuclease III. The nicked non-mutant strand was then repolymerized with the deoxynucleotide triphosphates, using the mutant strand as a template. As a result, both DNA strands in the final product contained the desired mutations. The DNA was transformed into E. coli K12 strain TG1. Plaques were selected, grown in liquid culture, and the single-stranded DNA isolated. The DNA was sequenced by the method of Sanger et al., *Proc. Natl. Acad. Sci. USA*, 74, 5463–5467 (1977) to confirm that the desired mutants had been obtained.

B. Conversion of Amino Acids 6 and 7

In the next step, the 5'-end of the mutated v-sis gene was replaced with a synthetic DNA fragment which changed amino acids 6 and 7 from the v-sis to the human PDGF-B forms. This synthetic fragment also provided a translation-initiating ATG codon immediately preceding the codon for serine 1 of human PDGF-B, as well as providing sequences for binding to E. coli ribosomes and a restriction site for ligation into the desired E. coli expression vector (described below). The synthetic DNA fragment was ligated to the BglII site located at nucleotide 4061 of the v-sis gene (numbering system of Devare et al., ibid). Because a BglII site which is present within the M13mp19 vector would complicate and interfere with this step, the mutated v-sis gene was first moved to the commercially available plasmid vector pUC18, which does not contain a BglII site. The M13mp19/v-sis mutant RF DNA was restricted with SalI and BamH1, and the resulting 1193 base pair fragment isolated by electrophoresis using a low meltite temperature agarose gel. This fragment was ligated to the plasmid pUC18 which had also been restricted with SalI and BamH1. The ligated DNA was transformed into the commercially available E. coli K12 strain DH5 and transformants were selected by growth in the presence of ampicillin. Colonies were selected, grown in liquid culture, and isolated plasmid DNA analyzed by restriction mapping for the presence of the v-sis insert.

The pUC18/v-sis mutant DNA was restricted with HindIII, which cuts in the polylinker of pUC18 just upstream of the mutated v-sis insert, and with BglII, which cuts within the v-sis DNA at nucleotide 4061 (Numbering system of Devare et al., ibid) corresponding to amino acid number 24 of the mature protein product. The large 3365 base pair fragment resulting from this reaction was isolated by electrophoresis in a low melting temperature agarose gel. This fragment was ligated to a synthetic double-stranded DNA fragment having the sequence of SEQ ID NO. 5 and SEQ ID NO. 6:

5' AGCTTCTAGAAGGAGGAATAACATATGTCTCTGGGTTCGTTAACCATTGCG-
3'          AGATCTTCCTCCTTATTGTATACAGAGACCCAAGCAATTGGTAACGC-

-GAACCGGCTATGATTGCCGAGTGCAAGACACGAACCGAGGTGTTCGA     3'
-CTTGGCCGATACTAACGGCTCACGTTCTGTGCTTGGCTCCACAAGCTCTAG 5'

This synthetic DNA fragment contains a HindIII "sticky" end at its upstream (left) end and a BglII "sticky" end at its downstream (right) end. In addition, an XbaI site (TCTAGA) is present within the synthetic DNA just downstream of the HindIII "sticky" end, which allows subsequent restriction with XbaI for ligation into the XbaI site of an expression vector described below. The ligated DNA was transformed into E. coli K12 strain DH5, with transformants being selected by growth on ampicillin-containing medium. The plasmid DNAs from resulting colonies were analyzed by restriction mapping for the presence of the synthetic DNA fragment. At this point, the pUC18/v-sis construction contained a mutated v-sis gene, with amino acid number 6, 6, 101, and 107 changed to the human PDGF form, and its 5'-end altered to begin translation with an ATG codon immediately preceding serine 1.

C. Conversion of Amino Acid 114 and Placement of a Stop Codon at Amino Acid 120

In the next step, the codon for amino acid number 114 was changed from ACT to GGT, resulting in the substitution of glycine for threonine in the final protein product. In addition, codon number 120, in which GCC codes for alanine in v-sis, was changed to TAA, a translation termination codon. The resulting protein product of this construction ends with the arginine at residue 119. Both of the changes were accomplished in one step by insertion of a synthetic DNA fragment after a SmaI site located within codon number 112.

The pUC18/v-sis mutant DNA generated above was restricted with SmaI, which cuts at nucleotide 4324 in the v-sis sequence (numbering system of Devare et al., ibid), and with EcoRI, which cuts in the polylinker of pUC18 just downstream of the v-sis insert. A small fragment (510 base pairs) between the SmaI and EcoRI sites, coding for the C-terminal portion of the v-sis protein and a 3'- untranslated sequence, was removed by electrophoresis on a low melting temperature agarose gel. The large fragment (about 3530 base pairs) was ligated to a synthetic DNA fragment having the sequence of SEQ ID NO. 7 and SEQ ID NO. 8:

5' GGGGGGTTCCCAGGAGCAGCGATAAG       3'
3' CCCCCCAAGGGTCCTCGTCGCTATTCTTAA  5'

The GGT codon coding for the new glycine residue at position 114 and the TAA termination codon introduced at position 120 are underlined above. This synthetic DNA fragment contains a blunt end at its upstream (left) and for ligating to the blunt end created by restriction of the v-sis mutant sequence with SmaI, and an EcoRI "sticky" end at its downstream (right) end for ligating to the EcoRI end created by restriction of the pUC18 polylinker with EcoRI. The ligated DNA was transformed into *E. coli* K12 strain DH5, with transformants being selected by growth on ampicillin-containing medium. The plasmid DNAs from resulting colonies were analyzed for the presence of the synthetic DNA fragment by restriction mapping.

EXAMPLE 2

Construction of PDGF-B$_{109}$ Precursor Coding Sequence

A PDGF-B109 precursor coding sequence, SEQ ID NO. 3 shown in FIG. 4 and containing amino acids −84 to −1 of the pre-pro region of PDGF-B precursor protein and the first 109 amino acids of the mature PDGF-B sequence, was constructed using a combination of naturally occurring and synthetic nucleic acid sequences, with the naturally occurring v-sis gene being employed as a starting material.

Specifically, the PDGF-B$_{109}$ precursor coding sequence was derived as follows. The DNA from nucleotides 1 to 98 was a synthetic DNA fragment wherein nucleotides 1 to 5 coded for a SalI restriction site (for use in ligation of the completed coding sequence into a plasmid vector), and nucleotides 6-98 exactly matched the region of human PDGF-B starting with the translation-initiating ATG at amino acid −81, and ending with an in-frame SacI restriction site at amino acid −55.

The DNA from nucleotides 99 to 220 was derived from a SacI to BstXI fragment from the pre-pro region of v-sis (nucleotides 3833 to 3953 of simian sarcoma virus, Devare et al., ibid) corresponding to amino acids −54 to −13 of the PDGF-B pre-pro region. The sequence from nucleotide 221 to 269 was derived from a synthetic DNA fragment with a BstXI site at its upstream and a HpaI half-site at its downstream ends, which encoded the amino acid sequence of the human PDGF-B precursor protein from amino acid −12 to +5. The sequence from nucleotide 270 to 326 was derived from a synthetic DNA fragment, with a HpaI half-site at its upstream end and a BglII site at its downstream end, which encoded the amino acid sequence of the human PDGF-B protein from amino acid +6 to amino acid +24. The sequence between nucleotides 327 and 1087 was derived from a BglII to XbaI fragment of v-sis (nucleotides 4225 to 4820 of simian sarcoma virus, Devare et al., ibid) corresponding to amino acids +25 to +160 of human PDGF-B, as well as the entire 3'-untranslated region. The sequence of this latter v-sis fragment was altered by in vitro mutagenesis (as described earlier in Example 1 with respect to the PDGF-B$_{119}$ coding sequence) to convert nucleotide 557 from T to C, thereby converting isoleucine-101 of v-sis to threonine as in human PDGF-B, and to convert nucleotide 574 from G to C, thereby converting alanine-107 of v-sis to proline, as in human PDGF-B. In vitro mutagenesis was also used to convert nucleotide 583 from C to T, nucleotide 586 from A to T, nucleotide 587 from G to A, and nucleotide 588 from C to A, thereby creating two tandem translation termination codons after amino acid 109 of PDGF-B.

The composite DNA sequence encoding the PDGF-B precursor protein (PDGF-B109 preceded by the entire pre-pro region of the PDGF precursor protein) was cloned as a SalI to XbaI fragment into the commercially available plasmid pGEM3. The pGEM3 plasmid contains a SacI restriction site just downstream of the XbaI site. The pGEM3/PDGF-B109/precursor plasmid was used as a source for a SacI to SacI fragment, encoding amino acids −54 to −1 of the PDGF-B pre-pro region, amino acids 1 to 109 of the mature PDGF-B protein, and the 3'-untranslated RNA sequence of v-sis, in constructing the PDGF-B fusion dimer DNA sequence, as described in Example 3, below.

EXAMPLE 3

Construction of PDGF-B$_{119}$/pre-pro/109 Plasmid in pUC18 Vector

A. Insertion of PDGF-B$_{119}$ coding sequence plus synthetic joining-linker into pUC18

The PDGF-B$_{119}$ coding sequence from Example 1 and the PDGF-B$_{109}$ coding sequence from Example 2 were linked together through a spacer coding sequence to form a coding sequence for a PDGF-B$_{119}$B$_{109}$ fusion homodimer.

Figure 2B:
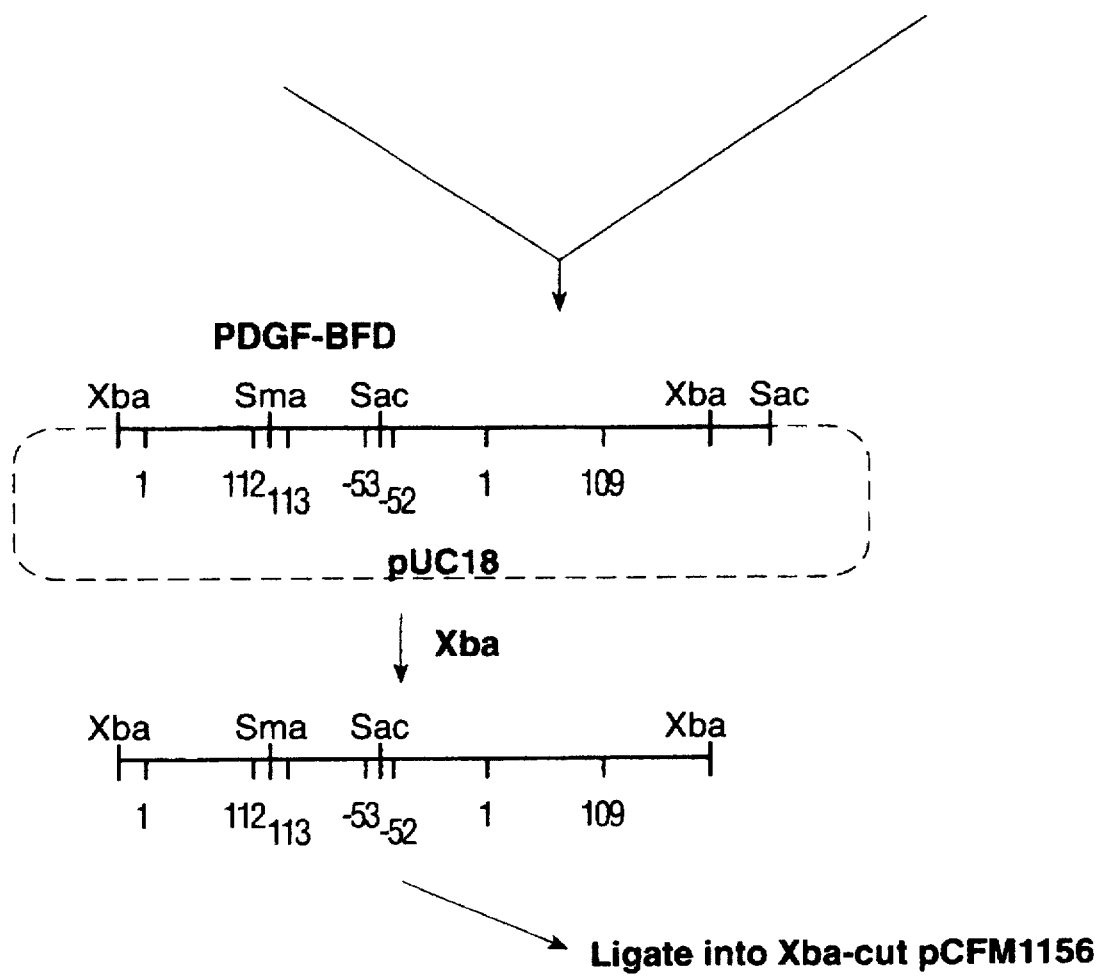

The precursor vector containing the PDGF-B$_{119}$ coding sequence was bacteriophage M13mp19. The single-stranded coding sequence was made double stranded by a standard in vitro reaction utilizing the Klenow fragment of *E. coli* DNA polymerase I. This double-stranded coding sequence was digested with the restriction enzymes XbaI and SmaI to release an approximately 380 base pair insert containing the PDGF-B$_{119}$ coding sequence up to the SmaI site at amino acid 112. Thus, the DNA encoding the last 7 amino acids was absent in this DNA fragment. The fragment was purified by electrophoresis through and extraction from a Seaplaque brand low-melting temperature agarose gel. The isolated PDGF-B$_{119}$ DNA fragment was mixed with a synthetic DNA linker containing a blunt-end SmaI half-site at its upstream end, and a SacI adapter site at its downstream end. The linker itself encoded amino acids 113-119 of the PDGF-B$_{119}$ monomeric unit plus amino acids number −54 and −53 of the pre-pro region of the PDGF-B precursor protein. The PDGF-B$_{119}$ DNA fragment plus the linker were ligated into the vector pUC18 which had been cut with XbaI and SacI. The ligated DNA was transformed into *E. coli* K-12 strain DH5α. (See FIG. 2.)

Plasmid DNA was isolated from several of the resulting transformant colonies, and the DNA inserts were analyzed by agarose gel electrophoresis. One plasmid with the correct insert was identified and utilized for the next step.

B. Insertion of the coding sequence for the spacer moiety and PDGF-B$_{109}$ subunit downstream of PDGF-B$_{119}$ subunit coding sequence and the linker A DNA segment encoding the amino acids number −52 to −1 of the pre-pro region of the PDGF-B precursor protein, plus amino acids number 1-109 of the mature PDGF-B sequence (PDGF-B$_{109}$), followed by two translation stop codons and the 3'-untranslated sequence of the v-sis gene, was inserted into the above construct at the SacI site. This was accomplished by first linearizing the above pUC18 construct containing the DNA encoding PDGF-B$_{119}$ and the linker with SacI. Next, a plasmid (pGEM3/PDGF-B$_{109}$/precursor) containing DNA coding for the entire PDGF-B precursor protein (with two stop codons following amino acid 109, so that the protein translation product was terminated after amino acid 109) was restricted with SacII. This restriction released a 1010 base pair fragment whose upstream end began with the codon for amino acid number −52 of the pre-pro region of the PDGF-B precursor protein, followed by the remainder of the protein coding region and the 3'-untranslated region, and whose downstream end contained part of the multiple cloning site of pGEM3. This fragment, encoding part of the pre-pro region of PDGF-B precursor protein as well as the 109 amino acid form of mature PDGF-B, was ligated into the SacI-cut pUC18/PDGF-B$_{119}$ construct described in Part A of this example. The ligation mixture was transformed into *E. coli* strain

15

DH5α, and plasmids from resulting colonies were analyzed by restriction analysis with the enzyme BglII. (See FIG. 2.)

EXAMPLE 4

Expression of PDGF-$B_{109}B_{109}$ Fusion Dimer in *E. coli*

The insert in pUC18 described in Example 3, coding for the PDGF-$B_{119}B_{109}$ fusion dimer with a pre-pro spacer, was removed from pUC18 by restriction with XbaI. The 1369 base pair XbaI fragment was purified by electrophoresis on a Seaplaque low-melting temperature agarose gel, and ligated into the *E. coli* expression vector pCFM1156. The plasmid pCFM1156PL is prepared from the known plasmid pCFM836. The preparation of plasmid pCFM836 is described in U.S. Pat. No. 4,710,473, the relevant portions of the specification, particularly examples 1 to 7, are hereby incorporated by reference. To prepare pCFM1156 and pCFM836, the two endogenous NdeI restriction sites are cut, the exposed ends are filled with T4 polymerase, and the filled ends are blunt-end ligated.

The resulting plasmid is then digested with ClaI and KpnI and the excised DNA fragment is replaced with a DNA oligonucleotide of the sequence of SEQ ID NO. 9:

5' ⟶ 3'

ClaI                                                                 KpnI
CGATTTGATTCTAGAAGGAGGAATAACATATGGTTAACGCGTTGGAATTCGGTAC
   TAAACTAAGATCTTCCTCCTTATTGTATACCAATTGCGCAACCTTAAGC

3' ⟶ 5'

The pCFM1156 vector contains a region for insertion of foreign genes between an upstream XbaI site and one of a number of downstream restriction sites. In this case, just the XbaI site was utilized.

The ligation mixture was transformed into *E. coli* strain FM-5 (ATCC NO. 53911), and transformants were analyzed by restriction mapping. A clone containing the insert fragment in the correct orientation was identified. The DNA insert present in this plasmid was subsequently sequenced, and the observed sequence matched the expected sequence coding for the protein having SEQ ID NO. 1, as shown in FIG. 1.

The final expression plasmid contained an inserted DNA sequence which codes for a protein that begins with an initiating methionine, followed by amino acids 1-119 of the human PDGF-B sequence, followed by a spacer of amino acids −54 to −1 of the pre-pro region of the human PDGF-B precursor protein sequence, followed by amino acids 1-109 of the human PDGF-B sequence. The procaryotic *E. coli* host cells removed the N-terminal methionine after synthesis, so that the final protein produced corresponds to the PDGF-$B_{119}B_{109}$ fusion homodimer having a spacer of 54 amino acids.

The *E. coli* clone containing the insert for the PDGF-$B_{119}B_{109}$ fusion dimer was grown in liquid culture at 30° C. for 2 hours, and then switched to the induction temperature of 42° C. for 4 hours. Aliquots of the cells before and after induction were lysed by boiling in SDS, and proteins were analyzed by SDS gel electrophoresis followed by staining with Coomassie Blue dye. A band of approximately the right predicted size (31 Kd) for the PDGF-$B_{119}B_{109}$ fusion dimer was observed in the lane derived from cells after induction,

16 which was not present in the lane from uninduced cells. Proteins were transferred from the gel to a nitrocellulose membrane via a Western blot procedure, and the blot was analyzed by incubation with an antibody to PDGF-B. The new protein in the induced cells containing the PDGF-$B_{119}B_{109}$ fusion dimer plasmid specifically reacted with the antibody, confirming that this protein was in fact the PDGF-$B_{119}B_{109}$ fusion dimer.

EXAMPLE 5

Mitogenic Activity of Unpurified PDGF-$B_{119}B_{109}$Fusion Dimer

As a first test for potential mitogenic activity of the PDGF-$B_{119}B_{109}$ fusion dimer, *E. coli* cells expressing the protein were lysed in a French press. The insoluble material, which included most of the PDGF-$B_{119}B_{109}$ fusion dimer protein, was pelleted by centrifugation. The pellet was solubilized in 0.8 ml of 6M guanidine HCl, then diluted into 8 ml of 50 mM Tris HCl, pH 8.0. It was estimated by electrophoretic analysis that this sample contained about 30 μg/ml of the PDGF-$B_{119}B_{109}$ fusion dimer. This material was analyzed at several concentrations for mitogenic stimulation of NRK fibroblasts. A dose-dependent stimulation was observed, with maximum stimulation occurring at a PDGF-$B_{119}B_{109}$ fusion dimer dose of approximately 34 ng/ml. This was the first demonstration that the protein was biologically active, and even when "folded" by this crude procedure, the level of activity was comparable to that of wild-type PDGF-BB.

EXAMPLE 6

Purification and Refolding of PDGF-$B_{119}B_{109}$ Fusion Dimer

Cells from the *E. coli* fermentation medium of Example 5, containing PDGF-$B_{119}B_{109}$ fusion homodimer, were purified in two batches. In both cases, the cells were first suspended in about 10 volumes (wet weight/volume) of water, and then passed three times through a Gaulin homogenizer of 9000 psi. The homogenized cells were then centrifuged at 5000×g for 1 hour at 4° C., and the supernatant discarded.

The resulting precipitate (inclusion bodies containing PDGF-$B_{119}B_{109}$ fusion homodimer) was suspended in 6M guanidine-HCl, 100 mM Tris chloride, pH 7.5 at a volume of about 60% of the volume of water used for the first cell suspension. β-mercaptoethanol was added to a concentration of about 0.08% (v/v), and the suspension mixed for 90 minutes at ambient temperature. Five volumes of water were slowly added over about 15 minutes, mixing continued for about 16 hours at ambient temperature. Water was slowly added to bring the guanidine-HCl concentration to 0.6M. The pH was adjusted to about 3.5 with acetic acid and mixed at 4° C. for about 3 hours. The suspension was then centrifuged at 17,700×g for 15 minutes at 4° C. to clarify the mixture. The resulting supernatant was then loaded onto an S-Sepharose® column (Pharmacia Biotech, Piscataway, N.J.) equilibrated with 0.1M sodium acetate, pH 4. The loaded column was washed with: (1) 20 mM sodium phosphate, pH 7.5; then (2) 20 mM sodium phosphate, pH 7.5, 0.1M sodium chloride; and then (3) 20 mM sodium phosphate, pH 7.5, 1.0M sodium chloride.

The fractions in the last wash, containing the PDGF-$B_{119}B_{109}$ fusion homodimer, were pooled and applied to an immunoaffinity column containing a monoclonal antibody recognizing PDGF-BB. The loaded affinity column was washed with: (1) 0.5M sodium chloride, 25 mM Tris-chloride, pH 7.5; and then (2) 0.5M sodium chloride. PDGF-$B_{119}B_{109}$ fusion homodimer was then eluted with 1M acetic acid, 0.15M sodium chloride, and concentrated over an Amicon®-YM10 (Amicon, Beverly, Massachusetts) membrane solvent-exchanged with water.

The PDGF-$B_{119}B_{109}$ fusion homodimer was then applied to a polysulfoethyl aspartamide column (The Nest Group, South Boro, Mass.) and developed with a linear gradient of 0 to 1M sodium chloride in 20 mM sodium phosphate, pH 6.8. Those fractions containing the PDGF fusion dimer were pooled, concentrated, and then exchanged into 10 mM sodium acetate, pH 4/0.15M sodium chloride.

EXAMPLE 7

Mitogenic Activity of Purified and Folded PDGF-$B_{119}B_{109}$ Fusion Dimer

The first batch of purified PDGF-$B_{119}B_{109}$ fusion dimer from Example 6 was assayed for mitogenic activity on NRK cells, and was found to have activity similar to that of wild-type PDGF-BB.

Figure 5:
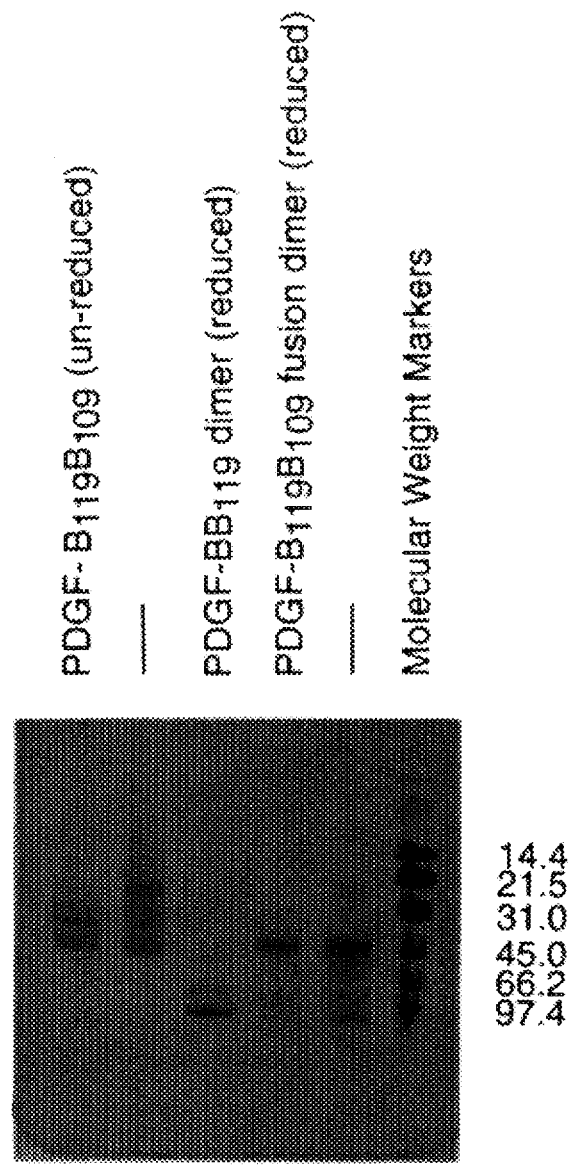
FIG. 5 is an electrophoretic gel of the PDGF-$B_{119}B_{109}$ fusion dimer whose amino acid sequence is shown in FIG. 1.
Figure 6:
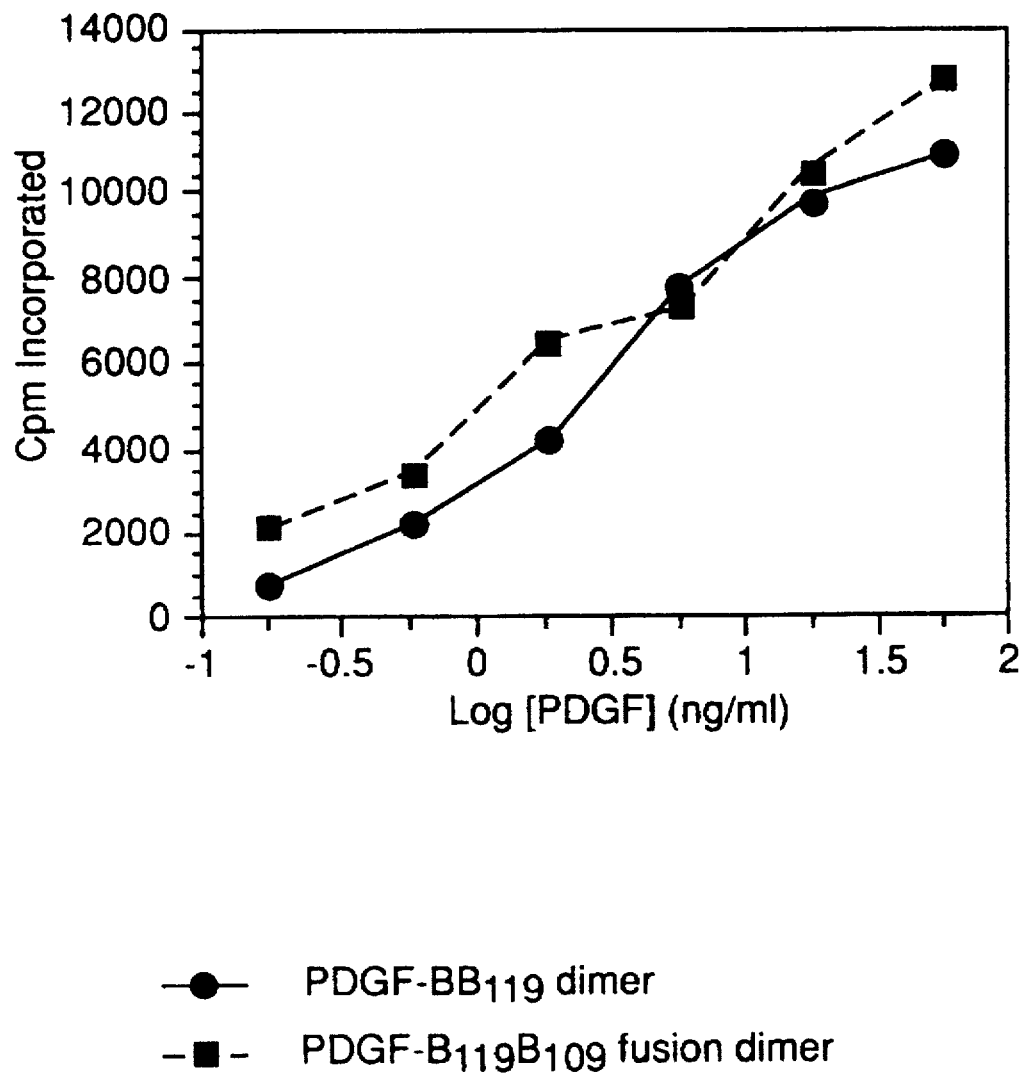
FIG. 6 is a graph showing the activity of the PDGF-$B_{119}B_{109}$ fusion dimer as compared to PDGF-$BB_{119}$.

The second batch of purified PDGF-$B_{119}B_{109}$ fusion dimer from Example 6 was analyzed by gel electrophoresis and for mitogenic activity on NRK cells. The protein ran as a dimer of approximately 31 Kd before and after reduction, indicating that the protein is a true fusion dimer, as shown in FIG. 5 The dose-response curves in the NRK mitogenic activity assay of the PDGF-$B_{119}B_{109}$ fusion dimer and of wild-type PDGF-BB homodimer were very similar, as shown in FIG. 6.

What is claimed is:

1. A biologically active protein comprising two subunits separated by a spacer moiety and forming a single continuous polypeptide wherein each subunit is a member of the PDGF family and wherein the spacer moiety is selected from the pre-pro region of a PDGF precursor protein.

2. The biologically active protein of claim 1 wherein each of said subunits is selected from the group consisting of PDGF-A and PDGF-B.

3. The biologically active protein of claim 2 wherein both of said subunits is human PDGF-B.

4. The biologically active protein of claim 3 wherein said spacer moiety is the entire pre-pro region of the PDGF precursor protein.

5. The biologically active protein of claim 3 having the amino acid sequence of SEQ ID NO: 1.

6. A pharmaceutical composition comprising the biologically active protein of claim 1 and a pharmaceutically acceptable carrier.

7. The pharmaceutical composition of claim 6 wherein said spacer moiety is the entire pre-pro region of the PDGF precursor protein.

8. A nucleic acid sequence encoding a biologically active protein comprising two subunits separated by a spacer moiety and forming a single continuous polypeptide wherein each subunit is a member of the PDGF family and wherein the spacer moiety is selected from the pre-pro region of a PDGF precursor protein.

9. The nucleic acid sequence of claim 8 wherein each of said subunits is selected from the group consisting of PDGF-A and PDGF-B.

10. The nucleic acid sequence of claim 9 wherein both of said subunits is human PDGF-B.

11. The nucleic acid sequence of claim 10 wherein said spacer moiety is the entire pre-pro region of the PDGF precursor protein.

12. The nucleic acid sequence of claim 10 encoding the amino acid sequence of SEQ ID NO: 1.

13. A transfected host cell containing a nucleic acid sequence encoding a biologically active protein comprising two subunits separated by a spacer moiety and forming a single continuous polypeptide wherein each subunit is a member of the PDGF family and wherein the spacer moiety is selected from the pre-pro region of a PDGF precursor protein.

14. The transfected host cell of claim 13 wherein each of said subunits is selected from the group consisting of PDGF-A and PDGF-B.

15. The transfected host cell of claim 14 wherein both of said subunits is human PDGF-B.

16. The transfected host cell of claim 15 wherein said spacer moiety is the entire pre-pro region of the PDGF precursor protein.

17. The transfected host cell of claim 15 wherein the nucleic acid sequence encodes the amino acid sequence of SEQ ID NO: 1.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 282 amino acid residues
        ( B ) TYPE: amino acid
        ( C ) STRANDEDNESS:
        ( D ) TOPOLOGY: linear ( i i ) MOLECULE TYPE: polypeptide ( i i i ) SEQUENCE DESCRIPTION: SEQ ID NO:1:

```
Ser  Leu  Gly  Ser  Leu  Thr  Ile  Ala  Glu  Pro  Ala  Met
  1              5                        10

Ile  Ala  Glu  Cys  Lys  Thr  Arg  Thr  Glu  Val  Phe  Glu
              15                        20

Ile  Ser  Arg  Arg  Leu  Ile  Asp  Arg  Thr  Asn  Ala  Asn
 25                        30                        35

Phe  Leu  Val  Trp  Pro  Pro  Cys  Val  Glu  Val  Gln  Arg
                 40                        45

Cys  Ser  Gly  Cys  Cys  Asn  Asn  Arg  Asn  Val  Gln  Cys
         50                        55                        60

Arg  Pro  Thr  Gln  Val  Gln  Leu  Arg  Pro  Val  Gln  Val
                      65                        70

Arg  Lys  Ile  Glu  Ile  Val  Arg  Lys  Lys  Pro  Ile  Phe
              75                        80

Lys  Lys  Ala  Thr  Val  Thr  Leu  Glu  Asp  His  Leu  Ala
 85                        90                        95

Cys  Lys  Cys  Glu  Thr  Val  Ala  Ala  Ala  Arg  Pro  Val
                100                       105

Thr  Arg  Ser  Pro  Gly  Gly  Ser  Gln  Glu  Gln  Arg  Glu
         110                       115                       120

Leu  Tyr  Lys  Met  Leu  Ser  Gly  His  Ser  Ile  Arg  Ser
                     125                       130
```

-continued

```
Phe  Asp  Asp  Leu  Gln  Arg  Leu  Leu  Gln  Gly  Asp  Ser
          135                      140
Gly  Lys  Glu  Asp  Gly  Ala  Glu  Leu  Asp  Leu  Asn  Met
145                      150                      155
Thr  Arg  Ser  His  Ser  Gly  Gly  Glu  Leu  Glu  Ser  Leu
               160                      165
Ala  Arg  Gly  Lys  Arg  Ser  Leu  Gly  Ser  Leu  Thr  Ile
          170                 175                      180
Ala  Glu  Pro  Ala  Met  Ile  Ala  Glu  Cys  Lys  Thr  Arg
                    185                      190
Thr  Glu  Val  Phe  Glu  Ile  Ser  Arg  Arg  Leu  Ile  Asp
          195                      200
Arg  Tyr  Asn  Ala  Asn  Phe  Leu  Val  Trp  Pro  Pro  Cys
205                           210                 215
Val  Glu  Val  Gln  Arg  Cys  Ser  Gly  Cys  Cys  Asn  Asn
               220                      225
Arg  Asn  Val  Gln  Cys  Arg  Pro  Thr  Gln  Val  Gln  Leu
     230                      235                      240
Arg  Pro  Val  Gln  Val  Arg  Lys  Ile  Glu  Ile  Val  Arg
                    245                      250
Lys  Lys  Pro  Ile  Phe  Lys  Lys  Ala  Thr  Val  Thr  Leu
          255                      260
Glu  Asp  His  Leu  Ala  Cys  Lys  Cys  Glu  Thr  Val  Ala
265                      270                      275
Ala  Ala  Arg  Pro  Val  Thr
                    280
```

( 2 ) INFORMATION FOR SEQ ID NO:2:

( i ) SEQUENCE CHARACTERISTICS:
        ( A ) LENGTH: 386 bases (upper strand)
        ( B ) TYPE: nucleic acid
        ( C ) STRANDEDNESS: double
        ( D ) TOPOLOGY: linear ( i i ) MOLECULE TYPE: other nucleic acid ( i i i ) SEQUENCE DESCRIPTION: SEQ ID NO:2:

```
CTAGAAGGAG  GAATAACAT  ATG  TCT  CTG  GGT  TCG  TTA  ACC           40
                      Met  Ser  Leu  Gly  Ser  Leu  Thr
                       1                  5

ATT  GCG  GAA  CCG  GCT  ATG  ATT  GCC  GAG  TGC  AAG  ACA         76
Ile  Ala  Glu  Pro  Ala  Met  Ile  Ala  Glu  Cys  Lys  Thr
               10                      15

CGA  ACC  GAG  GTG  TTC  GAG  ATC  TCC  CGG  CGC  CTC  ATC        112
Arg  Thr  Glu  Val  Phe  Glu  Ile  Ser  Arg  Arg  Leu  Ile
 20                      25                      30

GAC  CGC  ACC  AAT  GCC  AAC  TTC  CTG  GTG  TGG  CCG  CCC        148
Asp  Arg  Thr  Asn  Ala  Asn  Phe  Leu  Val  Trp  Pro  Pro
               35                      40

TGC  GTG  GAG  GTG  CAG  CGC  TGC  TCC  GGC  TGT  TGC  AAC        184
Cys  Val  Glu  Val  Gln  Arg  Cys  Ser  Gly  Cys  Cys  Asn
      45                      50                      55

AAC  CGC  AAC  GTG  CAG  TGC  CGG  CCC  ACC  CAG  GTG  CAG        220
Asn  Arg  Asn  Val  Gln  Cys  Arg  Pro  Thr  Gln  Val  Gln
               60                      65

CTG  CGG  CCA  GTC  CAG  GTG  AGA  AAG  ATC  GAG  ATT  GTG        256
Leu  Arg  Pro  Val  Gln  Val  Arg  Lys  Ile  Glu  Ile  Val
      70                      75
```

```
CGG AAG AAG CCA ATC TTT AAG AAG GCC ACG GTG ACG         292
Arg Lys Lys Pro Ile Phe Lys Lys Ala Thr Val Thr
 80              85                  90

CTG GAG GAC CAC CTG GCA TGC AAG TGT GAG ACA GTG         328
Leu Glu Asp His Leu Ala Cys Lys Cys Glu Thr Val
             95                 100

GCA GCT GCA CGG CCT GTG ACC CGA AGC CCG GGG GTT         364
Ala Ala Ala Arg Pro Val Thr Arg Ser Pro Gly Gly
        105             110             115

GGT TCC CAG GAG CAG CGA TAAG                            386
Ser Gln Glu Gln Arg
             120
```

( 2 ) INFORMATION FOR SEQ ID NO:3:

( i ) SEQUENCE CHARACTERISTICS:
      ( A ) LENGTH: 588 bases
      ( B ) TYPE: nucleic acid
      ( C ) STRANDEDNESS: single
      ( D ) TOPOLOGY: linear ( i i ) MOLECULE TYPE: other nucleic acid ( i i i ) SEQUENCE DESCRIPTION: SEQ ID NO:3:

```
TC GACAGTCGGC ATG AAT CGC TGC TGG GCG CTC TTC           36
              Met Asn Arg Cys Trp Ala Leu Phe
               1               5

CTG TCT CTC TGC TGC TAC CTG CGT CTG GTC AGC GCC         72
Leu Ser Leu Cys Cys Tyr Leu Arg Leu Val Ser Ala
         10              15               20

GAG GGG GAC CCC ATT CCC GAG GAG CTC TAT AAG ATG         108
Glu Gly Asp Pro Ile Pro Glu Glu Leu Tyr Lys Met
                 25              30

CTG AGT GGC CAC TCG ATT CGC TCC TTC GAT GAC CTC         144
Leu Ser Gly His Ser Ile Arg Ser Phe Asp Asp Leu
         35              40

CAG CGC CTG CTG CAG GGA GAC TCC GGA AAA GAA GAT         180
Gln Arg Leu Leu Gln Gly Asp Ser Gly Lys Glu Asp
 45              50              55

GGG GCT GAG CTG GAC CTG AAC ATG ACC CGC TCC CAT         216
Gly Ala Glu Leu Asp Leu Asn Met Thr Arg Ser His
        60              65

TCT GGT GGC GAG CTG GAG AGC TTG GCT CGT GGG AAA         252
Ser Gly Gly Glu Leu Glu Ser Leu Ala Arg Gly Lys
        70              75               80

AGG AGC CTG GGT TCG TTA ACC ATT GCG GAA CCG GCT         288
Arg Ser Leu Gly Ser Leu Thr Ile Ala Glu Pro Ala
             85              90

ATG ATT GCC GAG TGC AAG ACA CGA ACC GAG GTG TTC         324
Met Ile Ala Glu Cys Lys Thr Arg Thr Glu Val Phe
         95              100

GAG ATC TCC CGG CGC CTC ATC GAC CGC ACC AAT GCC         360
Glu Ile Ser Arg Arg Leu Ile Asp Arg Thr Asn Ala
105              110              115

AAC TTC CTG GTG TGG CCG CCC TGC GTG GAG GTG CAG         396
Asn Phe Leu Val Trp Pro Pro Cys Val Glu Val Gln
             120             125

CGC TGC TCC GGC TGT TGC AAC AAC CGC AAC GTG CAG         432
Arg Cys Ser Gly Cys Cys Asn Asn Arg Asn Val Gln
130              135              140

TGC CGG CCC ACC CAG GTG CAG CTG CGG CCA GTC CAG         468
Cys Arg Pro Thr Gln Val Gln Leu Arg Pro Val Gln
```

|     |     |     |     | 145 |     |     |     |     | 150 |     |     |     |
|-----|-----|-----|-----|-----|-----|-----|-----|-----|-----|-----|-----|-----|
| GTG | AGA | AAG | ATC | GAG | ATT | GTG | CGG | AAG | AAG | CCA | ATC | 504 |
| Val | Arg | Lys | Ile | Glu | Ile | Val | Arg | Lys | Lys | Pro | Ile |     |
|     |     | 155 |     |     |     |     | 160 |     |     |     |     |     |
| TTT | AAG | AAG | GCC | ACG | GTG | ACG | CTG | GAG | GAC | CAC | CTG | 540 |
| Phe | Lys | Lys | Ala | Thr | Val | Thr | Leu | Glu | Asp | His | Leu |     |
| 165 |     |     |     |     | 170 |     |     |     |     | 175 |     |     |
| GCA | TGC | AAG | TGT | GAG | ACA | GTG | GCA | GCT | GCA | CGG | CCT | 576 |
| Ala | Cys | Lys | Cys | Glu | Thr | Val | Ala | Ala | Ala | Arg | Pro |     |
|     |     |     | 180 |     |     |     |     | 185 |     |     |     |     |
| GTG | ACC | TGA | TAA |     |     |     |     |     |     |     |     | 588 |
| Val | Thr |     |     |     |     |     |     |     |     |     |     |     |
|     |     | 190 |     |     |     |     |     |     |     |     |     |     |

( 2 ) INFORMATION FOR SEQ ID NO:4:

( i ) SEQUENCE CHARACTERISTICS:
        ( A ) LENGTH: 34 bases
        ( B ) TYPE: nucleic acid
        ( C ) STRANDEDNESS: single
        ( D ) TOPOLOGY: linear ( i i ) MOLECULE TYPE: other nucleic acid ( i i i ) SEQUENCE DESCRIPTION: SEQ ID NO:4:

GGTCACAGGC CGTGCAGCTG CCACTGTCTC ACAC          34

( 2 ) INFORMATION FOR SEQ ID NO:5:

( i ) SEQUENCE CHARACTERISTICS:
        ( A ) LENGTH: 98 bases (upper strand)
        ( B ) TYPE: nucleic acid
        ( C ) STRANDEDNESS: double
        ( D ) TOPOLOGY: linear ( i i ) MOLECULE TYPE: other nucleic acid ( i i i ) SEQUENCE DESCRIPTION: SEQ ID NO:5:

AGCTTCTAGA AGGAGGAATA ACATATGTCT CTGGGTTCGT      40

TAACCATTGC GGAACCGGCT ATGATTGCCG AGTGCAAGAC      80

ACGAACCGAG GTGTTCGA      98

( 2 ) INFORMATION FOR SEQ ID NO:6:

( i ) SEQUENCE CHARACTERISTICS:
        ( A ) LENGTH: 98 bases (lower strand)
        ( B ) TYPE: nucleic acid
        ( C ) STRANDEDNESS: double
        ( D ) TOPOLOGY: linear ( i i ) MOLECULE TYPE: other nucleic acid ( i i i ) SEQUENCE DESCRIPTION: SEQ ID NO:6:

AGATCTTCCT CCTTATTGTA TACAGAGACC CAAGCAATTG      40

GTAACGCCTT GGCCGATACT AACGGCTCAC GTTCTGTGCT      80

TGGCTCCACA AGCTCTAG      98

( 2 ) INFORMATION FOR SEQ ID NO:7:

( i ) SEQUENCE CHARACTERISTICS:
        ( A ) LENGTH: 26 bases (upper strand)
        ( B ) TYPE: nucleic acid
        ( C ) STRANDEDNESS: double
        ( D ) TOPOLOGY: linear (i i) MOLECULE TYPE: other nucleic acid (x i) SEQUENCE DESCRIPTION: SEQ ID NO:7:

GGGGGGTTCC CAGGAGCAGC GATAAG                                    26

(2) INFORMATION FOR SEQ ID NO:8:

(i) SEQUENCE CHARACTERISTICS:
        (A) LENGTH: 30 bases (lower strand)
        (B) TYPE: nucleic acid
        (C) STRANDEDNESS: double
        (D) TOPOLOGY: linear (i i) MOLECULE TYPE: other nucleic acid (x i) SEQUENCE DESCRIPTION: SEQ ID NO:8:

CCCCCCAAGG GTCCTCGTCG CTATTCTTAA                                30

(2) INFORMATION FOR SEQ ID NO:9:

(i) SEQUENCE CHARACTERISTICS:
        (A) LENGTH: 55 bases (upper strand)
        (B) TYPE: nucleic acid
        (C) STRANDEDNESS: double
        (D) TOPOLOGY: linear (i i) MOLECULE TYPE: other nucleic acid (i i i) SEQUENCE DESCRIPTION: SEQ ID NO:9:

CGATTTGATT CTAGAAGGAG GAATAACATA TGGTTAACGC                     40

GTTGGAATTC GGTAC                                                55